US007858612B2

(12) United States Patent
Ninomiya et al.

(10) Patent No.: US 7,858,612 B2
(45) Date of Patent: Dec. 28, 2010

(54) THERAPEUTIC AGENT FOR INFLAMMATORY BOWEL DISEASES

(75) Inventors: Tomohisa Ninomiya, Kawasaki (JP); Takashi Shishikura, Yokohama (JP); Mitsuhiro Uchida, Kawasaki (JP); Sho Takahata, Yokohama (JP); Yukari Hoshina, Ebina (JP); Ken-ichi Kawano, Hamamatsu (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 12/449,371

(22) PCT Filed: Dec. 17, 2008

(86) PCT No.: PCT/JP2008/072999

§ 371 (c)(1),
(2), (4) Date: Aug. 5, 2009

(87) PCT Pub. No.: WO2009/078444

PCT Pub. Date: Jun. 25, 2009

(65) Prior Publication Data

US 2010/0130475 A1    May 27, 2010

(30) Foreign Application Priority Data

Dec. 18, 2007 (JP) ............................ 2007-326543

(51) Int. Cl.
*A61K 31/5517* (2006.01)
(52) U.S. Cl. .................................. 514/212.06; 514/217
(58) Field of Classification Search .................. None
See application file for complete search history.

(56) References Cited

U.S. PATENT DOCUMENTS

| 5,686,442 | A | 11/1997 | Ohtsuka et al. |
| 5,840,895 | A * | 11/1998 | Ohtsuka et al. ............ 544/366 |
| 6,093,714 | A | 7/2000 | Ohtsuka et al. |
| 6,372,735 | B1 | 4/2002 | Ohtsuka et al. |

FOREIGN PATENT DOCUMENTS

| EP | 0686636 | 12/1995 |
| EP | 1026167 | 8/2000 |
| EP | 1650266 | 4/2006 |
| WO | 95/18130 | 7/1995 |
| WO | 97/00258 | 1/1997 |
| WO | 99/16770 | 4/1999 |
| WO | 02/44183 | 6/2002 |

OTHER PUBLICATIONS

The Merck Manual, 17th edition, (1999), pp. 307-311.*
International Search Report dated Jan. 20, 2009 in the International (PCT) Application PCT/JP2008/072999 of which the present application is the U.S. National Stage.
Keiichi Mitsuyama, "Kaiyosei Daichoen Chiryo no Saikin no Wadai", Japanese Journal of Gastroenterology, vol. 97, No. 1, pp. 10-20, 2000.
Hideo Yamazaki et al., "Kaiyosei Daichoen ni Taisuru Ko Allergy-zai no Koka", Gastroenterology, vol. 15, No. 2, pp. 135-140, 1991.
Notification of Reason for Rejection mailed May 15, 2009, in Japanese Patent Application No. 2009-510216, with English translation.
Keiichi Mitsuyama, "Recent Topic on Treatment of Ulcerative Colitis", Japanese Journal of Gastroenterology, vol. 97, No. 1, pp. 10-20, 2000, with English translation.
Hideo Yamazaki et al., "Effect of Anti-Allergic Drugs Against Ulcerative Colitis", Gastroenterology, vol. 15, No. 2, pp. 135-140, 1991, with English translation.
Supplementary European Search Report issued Dec. 8, 2009 in corresponding European Application No. 08863206.
Patent Cooperation Treaty (PCT) International Preliminary Report on Patentability (PCT/IB/338, PCT/IB/373) and Written Opinion of the International Searching Authority (PCT/ISA/237) issued Jul. 20, 2010 in International Application No. PCT/JP2008/072999, of which the present application is the U.S. National Stage.

* cited by examiner

*Primary Examiner*—Phyllis G. Spivack
(74) *Attorney, Agent, or Firm*—Wenderoth, Lind & Ponack, L.L.P.

(57) ABSTRACT

The present invention relates to a method for maintaining the remission of or treating inflammatory bowel diseases, which comprises administering a maintenance therapeutically effective amount or a therapeutically effective amount of 7,8-dimethoxy-4(5H),10-dioxo-1H-1,2,3-triazolo[4,5-c][1] benzoazepine, a prodrug thereof, or a pharmaceutically acceptable salt thereof to a mammal, wherein the prodrug is 2-(1-isopropoxycarbonyloxy-2-methylpropyl)-7,8-dimethoxy-4(5H),10-dioxo-2H-1,2,3-triazolo[4,5-c][1]benzoazepine. The method according to the present invention is effective in the maintenance therapy and therapy of the inflammatory bowel diseases and has few side effects. Particularly, the method according to the present invention may exhibit strong maintenance therapeutic and therapeutic effects, even on severe cases having resistance to the conventional therapeutics.

8 Claims, 2 Drawing Sheets

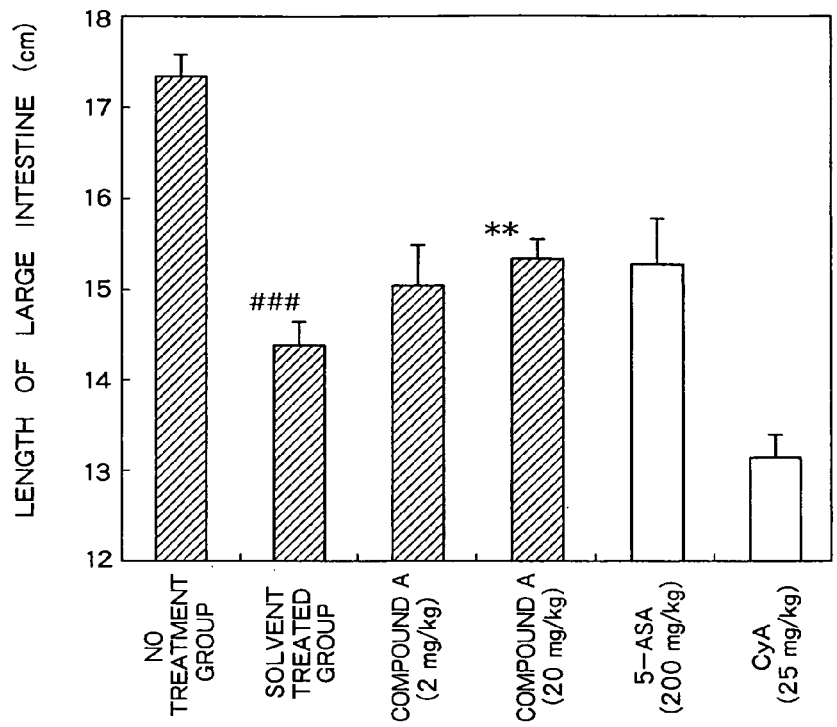
F I G. 1
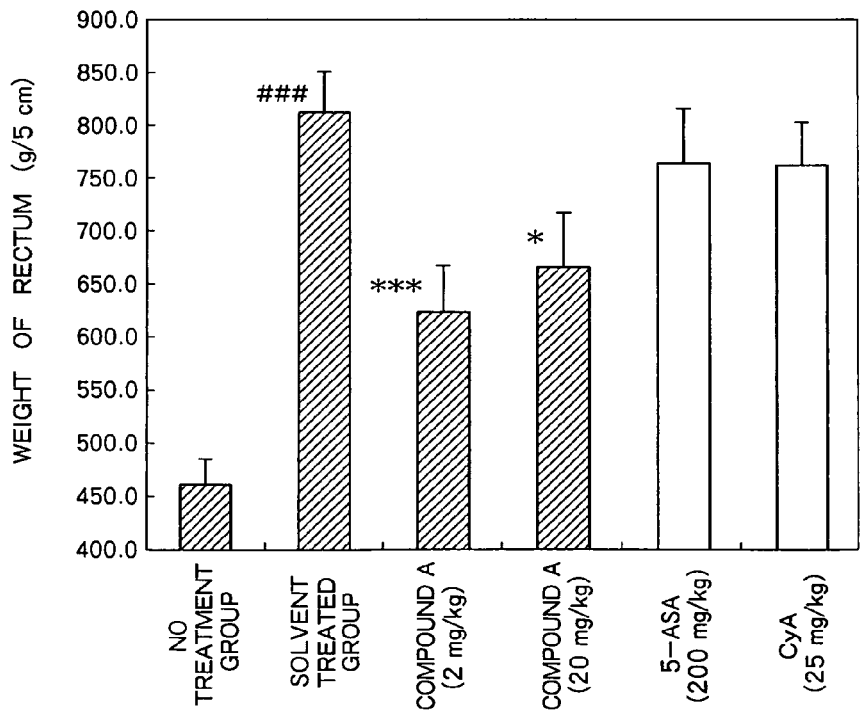
F I G. 2

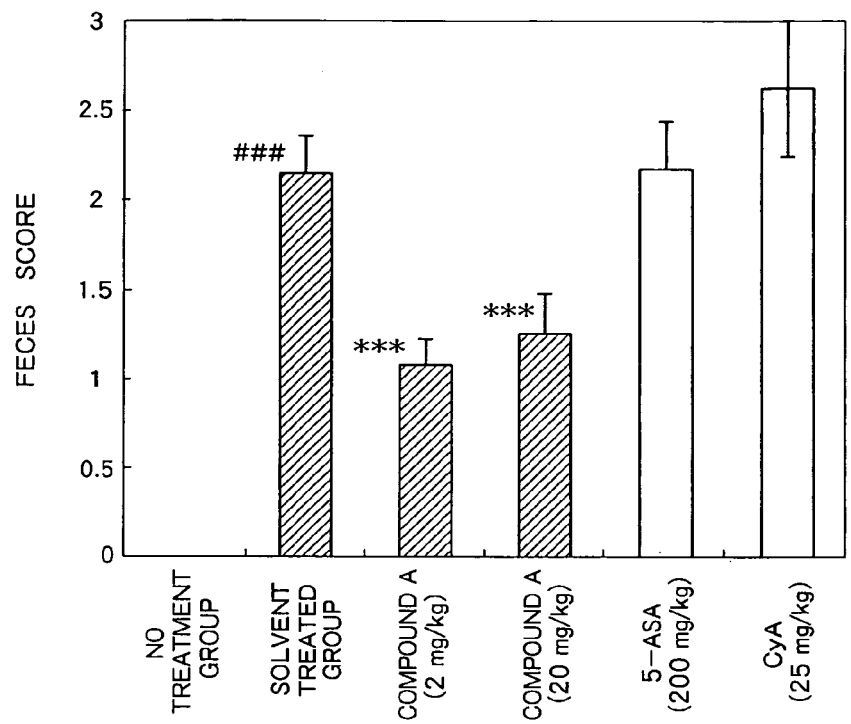
F I G. 3
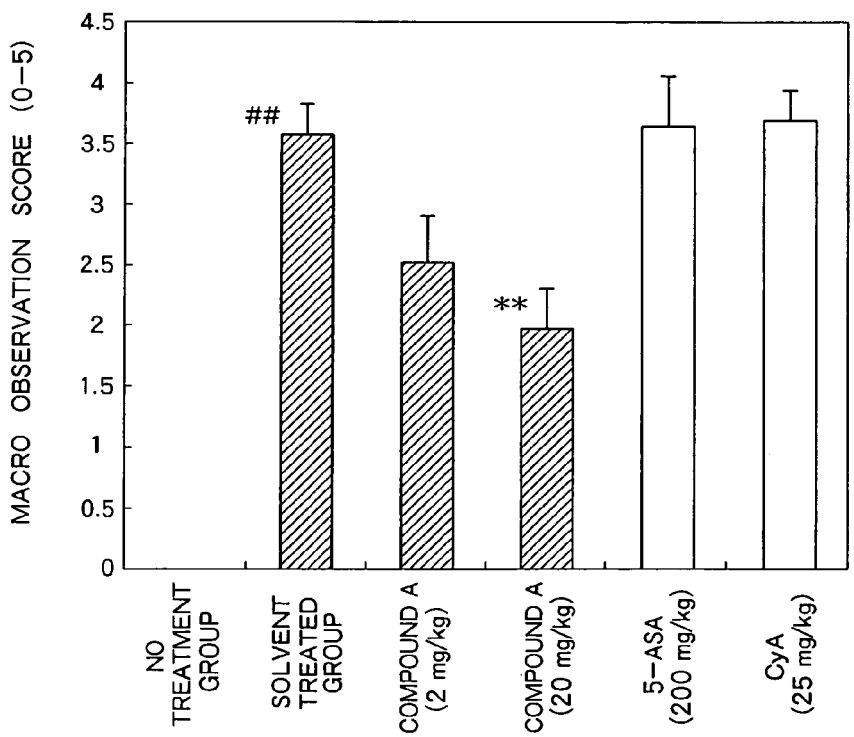
F I G. 4

THERAPEUTIC AGENT FOR INFLAMMATORY BOWEL DISEASES

CROSS-REFERENCE TO RELATED APPLICATION

This application is based upon and claims the benefit of priority from the prior Japanese Patent Application No. 2007-326543 (filed on Dec. 18, 2007), the entire contents of which are incorporated herein by reference.

BACKGROUND OF THE INVENTION

1. Field of the Invention

The present invention relates to a preventive or therapeutic agent for inflammatory bowel diseases such as ulcerative colitis and Crohn's disease. In particular, the present invention relates to a pharmaceutical composition for preventing or treating inflammatory bowel diseases, comprising 7,8-dimethoxy-4(5H),10-dioxo-1H-1,2,3-triazolo[4,5-c][1]benzoazepine, a prodrug thereof or a pharmaceutically acceptable salt thereof, or 2-(1-isopropoxycarbonyloxy-2-methylpropyl)-7,8-dimethoxy-4(5H),10-dioxo-2H-1,2,3-triazolo[4,5-c][1]benzoazepine or a pharmaceutically acceptable salt thereof.

2. Background Art

Inflammatory bowel disease (referred to hereinafter as "IBD") indicates idiopathic chronic persistent type non-specific enteritis, that is, typical diseases including ulcerative colitis, Crohn's disease (Koji Uraushibara, Mamoru Watanabe: "Concept, Definition and Epidemiology of Inflammatory Bowel Diseases"; Inflammatory Bowel Diseases, pp. 9-15, 2005, Ed. Norihumi Hibi; Saishin-Igaku (Reference 1). IBD is considered as a disease that the immunity mechanism of intestinal mucosa is collapsed by some etiologies to cause the excessive reaction with enterobacterium flora and bacterial components, which develops and sustains enteritis. However, the etiology of the disease has not been specified. It is known that in ulcerative colitis and Crohn's disease, which are the main diseases involved in IBD, the active phase in which symptoms such as ulceration and bleeding are expressed and the remission phase in which symptoms are remitted or ameliorated appear repeatedly, and it is believed that these diseases may recur over 10 to 20 years.

The critical mechanism of IBD has not been thoroughly elucidated yet.

Although allergy and infection theories were proposed for the explanation of the critical mechanism in the past, IBD is now considered as an autoimmune disease and studies which give support to the autoimmune theory including, for example, that the disease is accompanied with increased anti-neutrophil IgG antibody in blood have increased (Hibi N., Introduction Japanese J. Clin. Med., 63(5): 741-743, 2005 (Reference 2); Keiichi Mitsuyama, Makoto Toyonaga, and Michio Sata, "Pathology and Pathophysiology of Inflammatory Bowel Diseases"; Inflammatory Bowel Diseases, pp. 28-36, 2005, Ed. Norihumi Hibi; Saishin-Igaku (Reference 3). On the other hand, Ishizaka et al. have confirmed in 1966 the presence of the IgE antibody which is a causal antibody of allergy and demonstrated that the allergic reaction is a histamine releasing reaction mediated by the antigen specific IgE antibody (Mechanism of Body and Allergy, 1998 Shuichi Ueno, Nippon Jitsugyo Publishing (Reference 4); and Ishizaka K., Ishizaka T, and Hornbrook M M. Physico-Chemical Properties of Human Reaginic Antibody IV: Presence of a Unique Immunoglobulin as a Carrier of Reaginic Activity. Journal of Immunology, 97 (1): 75-85, 1966 (Reference 5)).

Thus, the allergy theory in IBD that the production of antigen-specific IgE antibody had not been observed became negative. It has also been confirmed that disodium cromoglycate (DSCG; Akihide Koda, "History and Present Situation of Anti-allergic Agents", pp. 32-39, 1988, Ed. Terumasa Miyamoto, Hiroshi Baba and Minoru Okuda, Life Science Co., Ltd. (Reference 6)), which was commonly approved as a typical histamine release inhibitor in three regions of Japan, United States of America and Europe, is ineffective against IBD (Crotty B and Jewell D P. Drug therapy of ulcerative colitis. Br. J. Clin. Pharmc. 34(3): 189-198, 1992 (Reference 7); Binder V, Elsborg L, Greibe J, Hendriksen C, Hoj L, Jensen K B, Kristensen E, Madsen J R, Marner B, Riis P, and Willumsen L. Disodium cromoglycate in the treatment of ulcerative colitis and Crohn's disease. 22 (1): 55-60, 1981 (Reference 8); and, Buckell N A, Gould S R, Day D W, Lennard-Jones J E, and Edwards A M. Controlled trial of disodium cromoglycate in chronic persistent ulcerative colitis. Gut, 19 (12): 1140-1143. 1978 (Reference 9)).

Under these circumstances, it has now generally been recognized that the allergic reaction is involved only seldom in critical mechanism of IBD both in clinical and basic studies.

Furthermore, it has recently been reported that inflammatory enteritis similar to IBD is spontaneously developed in IL-2 knockout mice and IL-10 knockout mice (Ma A, Datta M, Margosian E, Chen K and Horak I. T cells, but not B cells, are required for bowel inflammation in interleukin-2-deficient mice, J. Exp. Med. 182 (5): 1567-1572, 1995 (Reference 10); and, Kuhn R, Lohler J, Rennick D, Rajewsky K and Muller W. Interleukin-10-deficient mice develop chronic enterocolitis. Cell, 75(2): 263-274, 1993 (Reference 11)). The importance of abnormality of T cell-mediated immune reaction in manifestation of the disease has been indicated by the evidences that the defect of IL-2 having the T cell proliferating activity or IL-10 as a typical inhibitory cytokine caused IBD-like enteritis. That is, the crisis of enteritis is prevented in normal intestine by proliferating and activating T cells which suppress immune response against substances recognized as nonself including proteins derived from foods and foreign bodies derived from normal bacterial flora. However, it is considered that a certain immune system in topical intestinal mucosa is collapsed for some reason, which makes immune response uncontrollable to foreign bodies such as intestinal bacterial flora to which immune response is originally suppressed (Ohkusa T, Nomura T and Sato N., The role of bacterial infection in the pathogenesis of inflammatory bowel disease., International Medicine, 43(7): 534-539, 2004 (Reference 12), thus leading to the development of IBD. It is generally believed as described above that the immune abnormality centering around T cells is intensely involved in the critical mechanism of IBD (Tadao Baba, inflammatory bowel diseases, Recent Trend. Matsushita Medical Journal 39(1): 1-14, 2000 (Reference 13)).

Therapeutic object of IBD consists of induction of remission (alleviation of symptoms in the active phase) and preventing recurrence. While the therapeutic guidelines in respective countries do not reach complete consensus, a curative treatment commonly recommended in Japanese, US and British guidelines is as follows:

That is, 5-aminosalicylic acid (5-ASA) or sulfasalazine, which depends on the type, site and severity of disease of each patient, is employed as a standard therapeutic agent in treatment of mild to moderate patients. 5-ASA is a decomposition product of sulfasalazine and is believed the active substance of sulfasalazine. To moderate or severe patients, a steroid for oral or rectal dosage is also administered in addition to 5-ASA and sulfasalazine. In severe cases, remission is induced by the intravenous injection of steroid or an immune inhibitor cyclosporine. In recent years, the treatment with an anti-TNF-a-antibody and the like has been also carried out. 5-ASA and sulfasalazine are recommended for preventing recurrence after the induction of remission. Also, immunosuppressants such as azathiopurine (AZA) or 6-mercaptopurine (6-MP) are recommended for the prevention of recurrence.

However, 5-ASA and sulfasalazine widely used for the treatment of IBD often show insufficient therapeutic effects in moderate and severe patients. In such cases, remission is induced by using an immune inhibitor such as steroids or cyclosporine in serious patients in order to control abnormal reactions mainly caused by T cells, which are involved in the condition and severity of the diseases. Surgical excision of large intestine is performed on patients in refractory state in whom the induction of remission with these agents is difficult. It is known that if the treatment for preventing the recurrence is not performed after the induction of remission, that is, after the inflammation of the digestive tract has been ameliorated, IBD recurs or recrudesces in 70% of the patients. Therefore, it is also recommended in the guidelines to maintain the remission state (maintenance of remission) by continuing the prophylactic treatment for the recurrence. While the administration of 5-ASA or sulfasalazine is recommended for the maintenance of remission (prevention of recurrence), AZA or 6-MP is employed in the case that satisfactory effects are not obtained with 5-ASA or sulfasalazine. However, AZA and 6-MP require several months for the onset of effect, thus leaving the problem to be solved in their effectiveness.

Furthermore, the therapeutic agents such as steroids, cyclosporine, AZA or 6-MP exhibit strong systemic side effects, and thus there is a limitation on the use of them. By way of example, in addition to the side effects relating to immunodeficiency; steroids suppress osteogenesis or growth particularly in hebetic patients; cyclosporines cause renal disorders; AZA and 6-MP cause influenza-like symptoms and serious side effects such as bone marrow inhibition and hepatopathy. In addition, teratogenicity has been reported in animal experiments with steroids, cyclosporine, AZA and 6-MP, and thus safety in pregnancy and lactation has not been established, which limits the administration to female patients of the late teens to twenties who are predisposed to the development of IBD.

Under the circumstances described above, there has been in therapeutic fields a need for developing a novel drug for prophylactic treatment of inflammatory bowel diseases which can be safely and strongly induced into remission and used also in maintenance therapy for a long period of time.

2-(1-Isopropoxycarbonyloxy-2-methylpropyl)-7,8-dimethoxy-4(5H),10-dioxo-2H-1,2,3-triazolo[4,5-c][1]benzoazepine (referred to hereinafter as "Compound A"), and 7,8-dimethoxy-4(5H),10-dioxo-1H-1,2,3-triazolo[4,5-c][1]benzoazepine (referred to hereinafter as "Compound B") have the structures represented in the following:

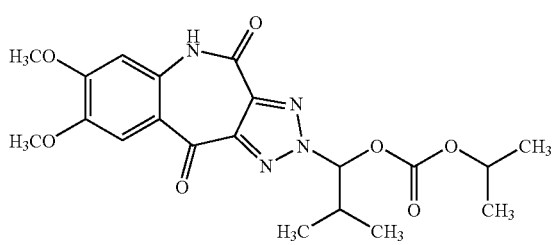

(Compound A)

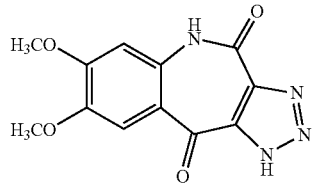

(Compound B)

It is known that Compound A is a prodrug of Compound B and is rapidly converted into Compound B in the body after permeating through various mucosae including digestive tracts, thus expressing histamine release inhibitory effect (see WO 95/18130 (JP 3,290,664-B, U.S. Pat. No. 5,686,442)). It has also been revealed that Compound A has an improved absorbability seven times as large as that of Compound B upon oral administration (see WO 99/16770 (JP 3,188,482-B, U.S. Pat. No. 6,372,735)).

However, the literature relates to the therapeutic or prophylactic agents of allergic diseases and provides or indicates none of inflammatory bowel diseases (IBD), which are believed to have little relationship with allergic diseases, or their prophylactic or therapeutic methods. Thus, no disclosure is necessarily found in examples.

SUMMARY OF THE INVENTION

The present inventors have now unexpectedly found that both of Compound A and Compound B are potently effective in the prophylaxis and therapy of inflammatory bowel diseases (IBD), and in particular, exhibit strong prophylactic and therapeutic effects also on severe cases having resistance to conventional therapeutics. In such situations that the allergic reaction is very rarely involved in critical mechanism of IBD as described above, Compound A and Compound B have extraordinarily exhibited prophylactic and therapeutic effects which are active to IBD. It has been unexpectedly suggested that Compound A and Compound B exhibit prophylactic and therapeutic effects which are active to IBD on the basis of the other reaction mechanism irrespective of their anti-allergic activities as confirmed also in examples described later. It has also been confirmed that each drug used in the treatment of IBD has at least either one of the activities: effectiveness in a carrageenin-induced inflammation model in rats; inhibition of the production of cytokine from leukocytes derived from the spleen. Specifically, it is a well known fact that sulfasalazine and steroids are effective in the carrageenin-induced inflammation model (Cronstein B N, Montesinos M C and Weissman G, Salitylates and sulfasalazine, but not glucocorticoid, inhibit leukocyte accumulation by an adenosine-dependent mechanism that is independent of inhibition of prostaglandin synthesis and p105 NF-κB, Proc. Natl. Acad. Sci. USA, May 25, 1999, 96(11): 6377-6381 (Reference 14)), and that steroids and immunosuppressants inhibit the production of cytokine from immunocytes such as T cells. On the other hand, it has been confirmed that Compound A or Compound B is ineffective in the carrageenin-induced inflammation model and has no activities on the production of cytokine from T cells derived from the spleen. That is, it has now been confirmed that the mechanism of exhibiting effective prophylactic and therapeutic activities on IBD by Compound A and Compound B is different from that of conventional therapeutics. These facts have also been found by the present inventors now. Furthermore, Compound A and Compound B have few side effects observed in the conventional preventive and therapeutic agent and are believed to be very useful for the prophylaxis and therapy of IBD. The present invention is based on these findings.

Thus, the object of the present invention is to provide a novel preventive and therapeutic agent for inflammatory bowel diseases which is effective for the prevention and treatment of inflammatory bowel diseases and has few side effects.

A pharmaceutical composition for preventing or treating inflammatory bowel diseases (IBD) according to the present invention comprises 7,8-dimethoxy-4(5H),10-dioxo-1H-1,2,3-triazolo[4,5-c][1]-benzoazepine (Compound B), a prodrug thereof, or a pharmaceutically acceptable salt thereof.

Also, a pharmaceutical composition for preventing or treating inflammatory bowel diseases (IBD) according to the present invention comprises 2-(1-isopropoxycarbonyloxy-2-methylpropyl)-7,8-dimethoxy-4(5H),10-dioxo-2H-1,2,3-triazolo[4,5-c][1]benzoazepine (Compound A), or a pharmaceutically acceptable salt thereof.

According to a preferred embodiment of the present invention, the pharmaceutical composition for preventing or treating inflammatory bowel diseases (IBD) is administered orally.

According to another preferred embodiment of the present invention, the pharmaceutical composition further comprises a pharmaceutically acceptable carrier.

According to one preferred embodiment of the present invention, the term "prevention" in the pharmaceutical composition for preventing or treating IBD means the prevention of recurrence of inflammatory bowel diseases.

According to a more preferred embodiment of the present invention, in the pharmaceutical composition, the inflammatory bowel disease is ulcerative colitis or Crohn's disease.

A method for preventing or treating inflammatory bowel diseases (IBD) according to the present invention comprises administering a prophylactically or therapeutically effective amount of 7,8-dimethoxy-4(5H),10-dioxo-1H-1,2,3-triazolo[4,5-c][1]benzoazepine, a prodrug thereof, or a pharmaceutically acceptable salt thereof to a mammal.

According to another preferred embodiment of the present invention, the method comprises administering a prophylactically or therapeutically effective amount of 2-(1-isopropoxycarbonyloxy-2-methylpropyl)-7,8-dimethoxy-4(5H),10-dioxo-2H-1,2,3-triazolo[4,5-c][1]benzoazepine, or a pharmaceutically acceptable salt thereof to a mammal.

Furthermore, according to the present invention, there is provided use of 7,8-dimethoxy-4(5H),10-dioxo-1H-1,2,3-triazolo[4,5-c][1]benzoazepine, a prodrug thereof, or a pharmaceutically acceptable salt thereof in the preparation of a preventive or therapeutic agent for inflammatory bowel diseases (IBD).

According to further another preferred embodiment of the present invention, there is provided use of 2-(1-isopropoxycarbonyloxy-2-methylpropyl)-7,8-dinnethoxy-4(5H),10-dioxo-2H-1,2,3-triazolo[4,5-c][1]-benzoazepine, or a pharmaceutically acceptable salt thereof in the preparation of a preventive or therapeutic agent for inflammatory bowel diseases (IBD).

Furthermore, in other words, the present invention can be said to provide (1) a preventive or therapeutic agent for inflammatory bowel diseases which comprises 2-(1-isopropoxycarbonyloxy-2-methylpropyl)-7,8-dimethoxy-4(5H),10-dioxo-2H-1,2,3-triazolo[4,5-c][1]benzoazepine, or a pharmaceutically acceptable salt thereof; and (2) a preventive or therapeutic agent for inflammatory bowel diseases which comprises 7,8-dimethoxy-4(5H),10-dioxo-1H-1,2,3-triazolo[4,5-c][1]benzoazepine, or a pharmaceutically acceptable salt thereof.

According to the present invention, a prophylactic or therapeutic pharmaceutical composition against inflammatory bowel diseases which has few side effects and exhibits strong prophylactic and therapeutic effects also on severe cases having resistance to conventional therapeutics can be obtained.

In this connection, it can be said that the "industrial availability" in the present invention consists in capability of providing a useful drug which is effective for the prophylaxis and therapy of inflammatory bowel diseases and has few side effects.

BRIEF DESCRIPTION OF THE DRAWINGS

FIG. 1 shows the experimental results of therapeutic effects of the respective agents on the shortening of large intestine by DSS procedure in Test Example 4 of Examples (###: $P<0.005$ vs. no procedure group (Student's t-test), **: $P<0.01$ vs. solvent treated group (Dunnett's multiple comparison test)).

FIG. 2 shows (###: $P<0.005$ vs. no procedure group (Student's t-test), ***: $P<0.005$, *: $P<0.05$ vs. solvent treated group (Dunnett's multiple comparison test)).

FIG. 3 shows the experimental results of therapeutic effects of the respective agents on the deterioration of fecal score in Test Example 4 of Examples (###: $P<0.005$ vs. no procedure group (Student's t-test), ***: $P<0.005$ vs. solvent treated group (Steel's multiple comparison test)).

FIG. 4 shows the experimental results of therapeutic effects of the respective agents on the deterioration of macro observation score in Test Example 4 of Examples (##: $P<0.01$ vs. no procedure group, **: $P<0.01$ vs. solvent treated group (Mann-Whitney's U-test)).

DETAILED DESCRIPTION OF THE INVENTION

Active Ingredients 7,8-Dimethoxy-4(5H),10-dioxo-1H-1,2,3-triazolo[4,5-c][1]benzoazepine, (Compound B), which is an active ingredient in the present invention, is a well known compound, and can be obtained according to the method described in the section relating to the process for preparing the compound and Example 43 WO 95/18130.

The active ingredient in the present invention may be a prodrug of Compound B or a pharmaceutically acceptable salt of the compound or a prodrug thereof. In this connection, the prodrug of Compound B is of a type that the 1,2,3-triazole group of Compound B has been modified, and can be prepared according to the process described in WO 99/16770.

2-(1-Isopropoxycarbonyloxy-2-methylpropyl)-7,8-dimethoxy -4(5H),10-dioxo-2H-1,2,3-triazolo[4,5-c][1]benzoazepine, (Compound A), which is an active ingredient in the present invention, is a well known compound, and can be obtained, for example, according to the method described in the section relating to the process for preparing the compound and Example 20 in WO 95/18130.

In the present invention, Compound A or Compound B as the active ingredients may be converted into pharmaceutically acceptable salts thereof, and such salts may be used as the active ingredients. The pharmaceutically acceptable salts of Compound A and Compound B include medically acceptable non-toxic salts. Such non-toxic salts preferably include alkali metal or alkaline earth metal salts such as sodium salt, potassium salt and calcium salt; hydrohalic acid salts such as hydrofluoric acid salt, hydrochloric acid salt, hydrobromic acid salt and hydroiodic acid salt; inorganic acid salts such as nitric acid salts, perchloric acid salts, sulfuric acid salts and phosphoric acid salts; organic acid salts such as methanesulfonic acid salt, fumaric acid salt, succinic salt, citric salt, tartaric acid salt, oxalic acid salt and maleic acid salt; and amino acid salts such as glutamic acid salt and aspartic acid salt.

Pharmaceutical Composition

Compound A and Compound B as the active ingredients in the present invention are known to have anti-allergic activities as described above.

However, it has now been confirmed that (i) these compounds have no direct inhibitory effect on the cytokine producing reaction from T cells which are believed as the central cell for inflammatory bowel diseases (IBD) (Test Example 8), and (ii) Compound A is ineffective in non-steroidal anti-inflammatory agents (such as indomethacin), sulfasalazine, or carrageenin induced inflammation model with which the effectiveness of steroids can be sensitively detected (Test Example 2).

In addition, as described above, the typical anti-allergic agent DSCG is ineffective in IBD. There are no cases so far as the present inventors know that indication for treatment of IBD has been approved with an anti-allergic agent having DSCG-like histamine release inhibitory effect or with an antagonist of histamine receptor.

These matters may suggest that Compound A and Compound B have less relationship to the reaction mechanism of a known IBD therapeutic agent, and that these compounds, even if having an anti-allergic activity, have little non-specific anti-inflammatory effect. It is also known as described above that the prophylactic and therapeutic effects on IBD have least relationship to the allergic reaction. It can be said that it was extremely difficult in such situations for a person skilled in the art to expect and anticipate the exertion of an effective prophylactic or therapeutic effect in itself. Therefore, it is believed that the prophylactic or therapeutic effect of Compound A and Compound B on IBD which has now been found in the present invention is unexpected and the characteristic function in Compound A and Compound B.

As will be described in Examples, it has been confirmed that when Compound A which is one of the active ingredients in the present invention was prophylactically administered orally to dextran sulfate sodium (DSS) induced IBD model rats, ulcerated area in rectum was reduced more largely than in treatment with sulfasalazine which was clinically formulated as a therapeutic agent routinely. Compound A also showed the effect equal to or more than steroid (prednisolone) without any side effects. On the other hand, significant weight gain inhibitory effect was observed as a side effect in the prednisolone treated group (Test Example 3). In other words, it has been confirmed that Compound A has actually prophylactic effects against IBD.

The IBD model is an animal model which corresponds to moderate to severe diseases and in which only sulfasalazine showed very slight inhibitory tendency. This is well consistent with clinical results.

Furthermore, when a DSS induced chronic IBD model was prepared and orally treated with Compound A or Compound B, respectively, the therapeutic effect on IBD and the dose dependent reaction were actually confirmed (Test Example 4). That is, as shown in Test Example 4, pathological conditions were significantly and dose-dependently inhibited in the administration of Compound A, and it was significantly inhibited in the administration of Compound B equally to Compound A under the condition that Compound A or Compound B was administered on and after three days of the administration of DSS (Test Example 5). Also, while the inhibition of weight gain was intensive to lead into the deterioration of whole symptoms in treatment with cyclosporine as an immune suppressant under the same condition, no therapeutic effects were obtained in treatment with 5-ASA. These results intensively suggested that Compound A and Compound B may be safe and strong oral therapeutics against IBD.

As the pathologic models of IBD, 2,4,6-trinitrobenzenesulphonic acid (TNBS) induced model is employed widely in addition to the DSS induced model. When the therapeutic effect and dose-dependent reaction of Compound A were examined in the TNBS induced IBD model, Compound A dose-dependently ameliorated colonic ulcer score on and after two days of TNBS procedure (Test Example 6). While significant ($P<0.01$) inhibition of weight gain (side effect) was observed in treatment with prednisolone used as a positive control compound, no such inhibition was observed in the Compound A treated group.

Furthermore, it has been confirmed that Compounds A and B used in the present invention have high safety because no abnormalities have been observed in repeated oral administration of the compounds for 26 consecutive weeks (Test Example 7).

Therefore, the active ingredients in the present invention exert excellent prophylactic or therapeutic effect against inflammatory bowel diseases (IBD), preferably by oral administration. Thus, according to the present invention, there is provided a prophylactic or therapeutic pharmaceutical composition against IBD, which comprises Compound B, prodrugs thereof or pharmaceutically acceptable salts thereof, or Compound A or pharmaceutically acceptable salts thereof.

The term "inflammatory bowel diseases" (IBD) hereby refers to non-specific enteritis of an idiopathic chronic persistent type, that is, typical diseases such as ulcerative colitis and Crohn's disease. Therefore, the term IBD excludes, according to the clinically general classification, infectious enteritis, pseudomembranous enteritis caused by antibiotics, ischemic enteritis, or peptic ulcer, or enteritis involved in general allergic reactions. Thus, according to the preferred embodiment of the present invention, inflammatory bowel disease is ulcerative colitis or Crohn's disease.

The term "prophylactic" or "preventive" hereby means complete or partial prevention of inflammatory bowel diseases or symptoms thereof in mammals, particularly human beings, and includes, for example, the prevention or inhibition of recurrence of inflammatory bowel diseases in patients who had previously been affected and treated.

In addition, the term "therapeutic" or "treatment" hereby means complete or partial curing of inflammatory bowel diseases or symptoms thereof, or furthermore malignancies caused thereby in mammals, particularly human beings. By way of example, the term "therapeutic" may include the inhibition of disease symptom, that is, the inhibition or delay of progress, the amelioration of disease symptom, that is, the regression of disease or symptom, or reversal of symptom progress.

The pharmaceutical composition according to the present invention can be administered orally or parenterally (for example, via intravenously, intramuscularly, rectally and transdermally), and can be used in a variety of dosage forms suitable for oral or parenteral administration in human beings and mammals other than human beings.

By way of example, the composition of the present invention can be prepared in any one of preparation (or formulation) forms including oral agents such as tablet, capsule, granules, powder, pill, fine particles, troche, syrup, and emulsion; injections such as intravenous and intramuscular injections; intrarectal agent, grease suppository, water soluble suppository, pastes such as ointment, and the like according to its applications. These preparations can be prepared by the conventional methods with usually used pharmaceutically acceptable carriers such as excipient, filler, binder, wetting agent, disintegrant, surfactant, humectant, dispersant, buffer, pH adjustor, conservation agent, chelator, dissolution accelerator, preservative, corrigent, soothing agent, stabilizer, and the like. The non-toxic additives which can be used include, for example, lactose, fructose, glucose, starch, gelatin, magnesium carbonate, synthetic magnesium silicate, talc, magnesium stearate, methyl cellulose, carboxymethyl cellulose or salts thereof, hydroxypropylmethyl cellulose, polyvinyl alcohol, polyvinylpyrrolidone, polyacrylic acid and salts thereof, gum arabic, olive oil, propylene glycol, polyethylene glycol, syrup, petrolatum, glycerin, ethanol, citric acid, sodium chloride, sodium sulfite, phosphate buffer, citrate buffer, tartrate buffer, acetate buffer, sodium phosphate, sodium hydroxide, ammonium hydroxide, hydrochloric acid, acetic acid, phosphoric acid, benzalconium chloride, benzethonium chloride, p-hydroxybenzoic acid esters such as methyl p-hydroxybenzoate or ethyl p-hydroxybenzoate, and the like.

The dosage of the pharmaceutical composition according to the present invention can be appropriately changed on the basis of the active ingredients contained therein, and prophylactically or therapeutically effective amounts of the active ingredients are administered to patients in order to prevent or treat the inflammatory bowel diseases as an object.

In this connection, the term "prophylactically or therapeutically effective amount" refers to an amount required for exerting the prophylactic or therapeutic effect on the aimed inflammatory bowel diseases in patients, and can be individually determined in consideration of the age, body weight, sex of a patient, diseases, level of symptoms, and the like.

When Compound A is employed in the present invention, the content of Compound A in the pharmaceutical composition may be varied according to its dosage forms and is generally in the concentration of 1 to 70% by weight, preferably 5 to 30% by weight. Specific methods for preparing the pharmaceutical composition are shown later in Preparation Examples. Dosages for preventing and treating IBD are appropriately determined in consideration of the usage, the age, sex of a patient, level of symptoms, and the like, and generally in the range of about 0.1 to 2000 mg per day for adults, preferably about 10 to 1000 mg, more preferably about 25 to 500 mg, which may be administered once or several portions a day.

When Compound B is employed, the content of Compound B in the pharmaceutical composition may be varied according to its dosage forms and is generally in the concentration of 1 to 70% by weight, preferably 5 to 30% by weight. Specific methods for preparing the pharmaceutical composition are shown later in Preparation Examples. Dosages for preventing and treating IBD are appropriately determined in consideration of the usage, the age, sex of a patient, level of symptom, and the like, and generally in the range of about 0.1 to 2000 mg per day for adult, preferably about 10 to 1000 mg, more preferably about 25 to 500 mg, which may be administered once or several portions a day.

Examples

The present invention is further illustrated by the following Examples that are not intended as a limitation of the invention.

Test Example 1

Test for Converting Compound A into Compound B

Male 8 week-old Wistar rats (purchased from Japan SLC, Inc.) under fasting conditions were orally administered with $^{14}C$ labeled Compound A at a dose of 1 mg/kg, and the amounts of Compound B in plasma, urine and bile were determined by Radio-HPLC.

As a result, Compound A was not detected in plasma 15 minutes after oral administration of Compound A, but Compound B was detected as the main metabolite. Also, Compound A was not detected in urine collected for 24 hours after administration of Compound A, but Compound B was detected as the main metabolite. Furthermore, Compound A was not detected in bile collected for 8 hours after administration of Compound A, but Compound B was detected as the main metabolite.

It was confirmed from the results described above that nearly all of Compound A was metabolized into Compound B when Compound A was absorbed into the body.

Test Example 2

Effects of Compound A and Indomethacin on Edema Induced in Rat Paws by Carrageenin To right hind paws of male 7 week-old Wistar rats (purchased from Japan SLC, Inc.) 0.1 ml of 1% λ-carrageenin was subcutaneously injected to cause paw edema reaction (n=5). Compound A at doses of 1 to 25 mg/kg and indomethacin at a dose of 5 mg/kg were orally administered 15 and 60 minutes before administration of carrageenin, respectively.

Three hours after administration of carrageenin, when the paw edema reaction reached maximum, the effectiveness was evaluated from the volumes of the right hind paw edema.

The results were obtained as shown in Table 1.

It was found from the results that Compound A at any doses exhibited no inhibitory effect, but indomethacin exhibited a significant ($p<0.01$) inhibitory effect.

TABLE 1

Effect of Compound A and indomethacin on carrageenin induced paw edema in rats

| Group | Volume of edema (ml) |
|---|---|
| Control | 0.82 ± 0.03 |
| Compound A, 1 mg/kg | 0.87 ± 0.04 |
| Compound A, 5 mg/kg | 0.89 ± 0.04 |
| Compound A, 25 mg/kg | 0.67 ± 0.05 |
| Indomethacin, 5 mg/kg | 0.48 ± 0.04** |

Mean ± SE **$P < 0.01$ vs control group

Test Example 3

Evaluation of Effectiveness in 3% Dextran Sulfate Sodium (DSS) Induced Acute Rat IBD Model (Prophylactic Effect)

A 3% dextran sulfate sodium (DSS) induced IBD model is one of the most useful IBD models.

IBD was induced by freely allowing male 7 week-old Wistar rats (purchased from Japan SLC, Inc.) to ingest 3% DSS solution (n=8). In the period of 7 days after initiating DSS administration, soft feces and blood feces scores were observed according to the following basis, and the sum of the soft feces score and blood feces score was obtained as the feces score of the individual animal.

Criteria:
  Soft feces score (0 to 3)
    [0: nothing abnormal detected (NAD),
    1: slightly soft,
    2: soft,
    3: diarrhea]
  Blood feces score (0 to 3)
    [0: nothing abnormal detected (NAD),
    1: blood in feces,
    2: bright-red blood adhered on feces,
    3: melena]

1% Evans blue physiological saline was intravenously injected in an amount of 1 ml per rat 8 days after DSS exposure, and the animal was euthanized 30 minutes after that for excising the large intestine. After immobilizing the large intestine in the length of 7 to 8 cm from anus with 4% formalin buffer for 20 minutes, the intestine was longitudinally opened from the mesenterium side for photographing the rectal portion. Ulcer area was calculated by image analysis.

Compound A (10 mg/kg/day), or. sulfasalazine (100 mg/kg/day) or prednisolone (1 mg/kg/day) as a control compound was made into suspension in an agate mortar, which was orally administered twice a day at a dose of 5 ml/kg to each rat starting from a day before administration of DSS to a day before dissection. In this connection, 1% hydroxypropylmethyl cellulose solution (HPMC) was used as a solvent, which was administered at a dose of 5 ml/kg to the solvent treated group.

The results were obtained as shown in Tables 2 and 3.

Specifically, Table 2 shows the results of effectiveness (inhibition rate) on feces score (mean±standard error) in the IBD model of each treated group, and Table 3 shows the results of ulcer area (mean±standard error) and its reduction effect (inhibition rate) in the IBD model of each treated group.

TABLE 2

Ulcer area reduction effect in DSS induced IBD model (inhibition rate)

| | Feces score | Inhibition rate (%) |
|---|---|---|
| No treatment group | 8.6 ± 3.6 | |
| Solvent treated group | 452.9 ± 60.9 | 0.0 |
| Sulfasalazine (100 mg/kg) treated group | 407.0 ± 30.9 | 8.2 |
| Prednisolone (1 mg/kg) treated group | 337.5 ± 34.1 | 26.1 |
| Compound A (10 mg/kg) treated group | 291.3 ± 37.0* | 36.4 |

*$P < 0.05$ vs solvent treated group

TABLE 3

Effectiveness on feces score in DSS induced IBD model (inhibition rate)

| | Feces score | Inhibition rate (%) |
|---|---|---|
| No treatment group | 0 ± 0 | |
| Solvent treated group | 3.38 ± 0.68 | 0.0 |
| Sulfasalazine (100 mg/kg) treated group | 2.63 ± 0.50 | 22.2 |
| Prednisolone (1 mg/kg) treated group | 2.00 ± 0.42 | 40.7 |
| Compound A (10 mg/kg) treated group | 2.00 ± 0.53 | 40.7 |

Test Example 4

Evaluation of Effectiveness of Compound A in DSS Induced Rat IBD Chronic Model (Therapeutic Effect)

Therapeutic effect of post-administration of Compound A was examined in the DSS induced model.

Colitis was induced by freely allowing male 7 week-old Wistar rats (purchased from Japan SLC, Inc.) to ingest 3% DSS solution for 3 days, and subsequently chronic IBD was induced by freely allowing to ingest 1% DSS solution starting from the 4th day of the test.

Compound A (2, 20 mg/kg/day), 5-aminosalicylic acid as a control (5-ASA: 200 mg/kg/day) and cyclosporine A (Cy A: 25 mg/kg/day) were administered to the animals starting from the 4th day of the test until the day of dissection (n=8 to 20).

The property of feces in individual animal was observed until the day before dissection, and the soft feces score and the blood feces score were determined according to the same basis as shown in Test Example 3 to obtain the sum of the soft feces score and blood feces score as the feces score.

Also, 1% Evans blue physiological saline was intravenously injected in an amount of 1 ml per rat on the day of dissection, and the animal was euthanized 30 minutes after that for excising the large intestine. After immobilizing the large intestine in the length of 7 to 8 cm from anus with 4% formalin buffer for 20 minutes, the intestine was longitudinally opened from the mesenterium side for photographing the rectal portion and measuring the rectum weight. The state and extent of eroded rectal portion were scored according to the following basis for making a macro observation score.

Criteria:
  Macro observation score (0-5)
    [0: normal,
    1: erosion formation in narrow ranges,
    2: weak erosion formation, without bleeding,
    3: moderate erosion formation and weak bleeding in narrow ranges,
    4: strong erosion formation and bleeding in narrow ranges,
    5: strong erosion formation and bleeding in wide ranges]

The results were obtained as shown in FIGS. 1, 2, 3 and 4.

Specifically, FIG. 1 shows the test results of the therapeutic effect of respective drugs on the shortening of large intestine due to the treatment with DSS, FIG. 2 shows the test results of the therapeutic effect of respective drugs on the increase of rectum weight, FIG. 3 shows the test results of the therapeutic effect of respective drugs on the deterioration of feces score on the day before dissection, and FIG. 4 shows the test results of the therapeutic effect of respective drugs on the increase of macro observation score, with mean ±standard error, respectively.

It has been confirmed from these results that a significant (P<0.01) ameliorating effect on the shortening of large intestine observed in the solvent treated group is exhibited by administration of Compound A (20 mg/kg/day) (FIG. 1), and that a significant (P<0.005, P<0.05) ameliorating effect on the significant increase of rectum weight observed in the solvent treated group is exhibited by administration of Compound A (2, 20 mg/kg/day) (FIG. 2).

In addition, a significant (P<0.005) ameliorating effect on the feces score on the day before dissection has been confirmed by administration of Compound A (2, 20 mg/kg/day) (FIG. 3).

Furthermore, it has been recognized in macro observation score as a result of evaluating it with the category test (U test) and the segmentation test (Fisher test) that a significant ameliorating effect (P=0.0006: category test, P=0.0003: segmentation test) was observed in the Compound A (20 mg/kg/day) treated group, and an inhibitory tendency (P=0.0509: category test, P=0.1161: segmentation test) was observed in the 2 mg/kg treated group (FIG. 4).

It has been confirmed from the results described above that Compound A has a dose-dependent therapeutic effect in the chronic IBD model. On the other hand, significant inhibitory effects were not recognized in any evaluation items for an immune suppressant Cy A and an anti-inflammatory agent 5-ASA.

Test Example 5

Evaluation of Effectiveness of Compound B in DSS Induced Rat IBD Chronic Model (Judgment of Therapeutic Effect)

A therapeutic effect of Compound B orally administered was examined in the same manner as in Test Example 4 except that Compound B (20 mg/kg/day) was used in place of Compound A (n=12).

As a result, while the feces score on the day before dissection was significantly (P<0.01) increased to 1.9±0.25 in the solvent treated group, in Compound B treated group significant (P<0.05) inhibition at 0.9±0.24 was recognized and an inhibitory effect was recognized in the macro observation score as well.

Test Example 6

Evaluation of Effectiveness in Trinitrobenzene Sulfonic Acid (TNBS) Induced Rat IBD Model (Therapeutic Effect)

A TNBS induced model as an animal model of IBD is widely used as a model of Crohn's disease. Thus, the TNBS induced model rats were employed for examining the therapeutic effect of Compound A.

8 week-old male SD rats (purchased from Charles River Laboratories Japan, Inc.) were intrarectally treated with TNBS to induce enteritis, and divided into groups 2 days after the treatment with TNBS to initiate the administration of the drugs. A solvent, Compound A (2, 20, 50 mg/kg/day), or prednisolone (6 mg/kg/day) was orally administered twice a day, and the rats were subjected to autopsy 8 days after administration for determining the macro observation score. The evaluation of the score was conducted by the method described in Table 4 according to the judgment method by JOHN L. WALLACE et al. (Gastroenterology 1989; 96: 29-36).

Furthermore, the large intestine was cut to a length of 10 cm for measuring the wet weight of intestine. The results of score evaluation are shown in Table 5, and the results of measuring the wet weight are shown in Table 6.

From these results, a significant increase in the macro observation score and an increase in the wet weight of large intestine were recognized in the solvent treated group. In contrast, significant (P<0.05) score amelioration and tendency to ameliorate the wet weight of large intestine were observed in the Compound A (50 mg/kg) treated group. Also, in the low-dose (2, 10 mg/kg) groups, the tendency to ameliorate the score was observed. On the other hand, a remarkable inhibition of (P<0.01) weight gain was observed in the prednisolone treated group as a positive control. In this connection, the significant inhibition of weight gain was not observed in the Compound A treated group.

TABLE 4

| Score | Criterion |
|---|---|
| 0 | No topical congestion, no bleeding, no ulcer |
| 1 | Topical congestion, bleeding, no ulcer |
| 2 | Ulcer involving congestion or hypertrophy of intestinal wall |
| 3 | Ulcer involving inflammation (one) |
| 4 | Ulcers at two or more sites, inflammation or geographic ulcer (ulcer width: less than 1 cm) |
| 5 | Ulcers at two or more sites, inflammation or geographic ulcer (ulcer width: 1 cm or more) |
| 6 | For the intestine, add 1 point per 1 cm of ulcer which exceeds 2 cm longitudinally |
| ~ | Add 1 point per 1 cm of ulcer horizontally |

TABLE 5

Effect on colonic ulceration score in TNBS induced IBD model

| Group | Dosage | No. of Cases | Colonic ulceration score |
|---|---|---|---|
| No treatment group | — | 6 | 0.0 ± 0.0 |
| Solvent treated group | — | 11 | 4.5 ± 0.3[##] |
| Compound A treated group | 1 mg/kg × 2 | 10 | 3.5 ± 0.4 |
| Compound A treated group | 5 mg/kg × 2 | 10 | 3.5 ± 0.5 |
| Compound A treated group | 25 mg/kg × 2 | 11 | 3.3 ± 0.3* |
| Prednisolone treated group | 3 mg/kg × 2 | 9 | 3.0 ± 0.5[b] |

[##]$P < 0.01$; no treatment group vs solvent treated group by Mann-Whitney test
*$P < 0.05$; solvent treated group vs Compound A treated group by Steel test
[b]$P < 0.05$; solvent treated group vs prednisolone treated group by Mann-Whitney test

TABLE 6

Effect on colonic wet weight of large intestine in TNBS induced IBD model

| Group | Dosage | No. of Cases | Colonic ulceration score |
|---|---|---|---|
| No treatment group | — | 6 | 0.70 ± 0.03 |
| Solvent treated group | — | 11 | 1.42 ± 0.09[##] |
| Compound A treated group | 1 mg/kg × 2 | 10 | 1.31 ± 0.08 |
| Compound A treated group | 5 mg/kg × 2 | 10 | 1.27 ± 0.08 |
| Compound A treated group | 25 mg/kg × 2 | 11 | 1.20 ± 0.04 |
| Prednisolone treated group | 3 mg/kg × 2 | 9 | 1.05 ± 0.09[bb] |

[##]$P < 0.01$; no treatment group vs solvent treated group by Mann-Whitney test
[bb]$P < 0.01$; solvent treated group vs prednisolone treated group by Steel test

Test Example 7

Twenty-Six Week Repeated Oral Administration Study of Compound A in Rats (Safety Test)

To 6 week-old male and female SD rats (purchased from Charles River Laboratories Japan, Inc.) a solvent (hydroxymethyl cellulose) or Compound A (100, 300, 1000 mg/kg/day) was administered orally and repeatedly for 26 consecutive weeks (n=15).

As a result, no abnormalities were observed in the general conditions, weight change, food consumption and histopathology in any dose groups.

It has been judged from these results that the No-Observed-Adverse-Effect-Level (NOAEL) of Compound A is 1000 mg/kg/day or more.

Test Example 8

Study of Direct Effect on the Activation of T Cells with Compound B 7 week-old male Balb/c mice (purchased from Japan SLC, Inc.) were sensitized with an aluminum hydroxide gel-ovalbumin suspension administered intraperitoneally or subcutaneously in both inguinal regions on the first and 14th days, and the spleen was excised on the 21st day for preparing a splenocyte suspension. After removal of erythrocytes, Compound B (10 µM) and ovalbumin were added to splenocytes suspended in a culture medium, and the mixture was cultured at 37° C. under a condition of 5% $CO_2$.

IL-4 in the supernatant after culture for 6 hours, and IL-2, IL-5 and IFNγ in the supernatant after culture for 24 hours were quantitatively determined by ELISA (ELISA kit manufactured by ENDOGEN).

As a result, while IL-4, IL-2, IL-5 and IFNγ were increased in the control group, Compound B did not inhibit the production of these cytokines. At this time, prednisolone almost completely inhibited IL-2, IL-5 and IFNγ, but not IL-4.

It is believed from the results described above that a pharmaceutical composition comprising Compound A and Compound B as the active ingredients is actually more potent than sulfasalazine or 5-ASA against IBD, and has a strong effectiveness equal to or more than prednisolone. Furthermore, it is believed that an oral drug comprising Compound A and Compound B as the active ingredients not only has prophylactic effects, but also can be expected to have therapeutic effects. It is also believed that since weight gain is conspicuously inhibited in the prednisolone treated group and the cyclosporine treated group and side effects such as inhibition of weight gain was not observed in the Compound A and Compound B treated groups, the oral drug comprising Compound A and Compound B as the active ingredients has high safety.

Examples of Drug Manufacture: Example Formulation of Prophylactic or Therapeutic Composition Against Inflammatory Bowel Diseases Preparation Examples of pharmaceutical compositions for preventing or treating inflammatory bowel diseases according to the present invention and formulation for preparing the compositions are shown below.

Preparation Example 1

Tablets

TABLE 7

| Compound A | 2.5 g |
| Hypromellose | 0.5 g |
| Lactose | 11.5 g |
| 6% HPC lactose | 8 g |
| Potato starch | 2 g |
| Magnesium stearate | 0.5 g |
| Total | 25 g |

Preparation Example 2

Capsules

TABLE 8

| Compound A | 2.5 g |
| Hypromellose | 0.5 g |
| Lactose | 17.5 g |
| Potato starch | 4 g |
| Magnesium stearate | 0.5 g |
| Total | 25 g |

Preparation Example 3

Enema

TABLE 9

| Compound B | 1.0 mg/ml |
| Tris(hydroxymethyl)aminomethane | 1.2 mg/ml |
| Carboxymethyl cellulose sodium | 15 mg/ml |
| Hydrochloric acid | q.v. |
| pH | 7.0 |

The invention claimed is:

1. A method for maintaining the remission of or treating inflammatory bowel diseases (IBD), which comprises administering a maintenance therapeutically effective amount or a therapeutically effective amount of 7,8-dimethoxy-4(5H),10-dioxo-1H-1,2,3-triazolo[4,5-c][1]benzoazepine, a prodrug thereof, or a pharmaceutically acceptable salt thereof to a mammal, wherein the prodrug is 2-(1-isopropoxycarbonyloxy-2-methylpropyl)-7,8-dimethoxy-4(5H),10-dioxo-2H-1,2,3-triazolo[4,5-c][1]benzoazepine.

2. A method according to claim 1, wherein the compound to be administered is 2-(1-isopropoxycarbonyloxy-2-methylpropyl)-7,8-dimethoxy-4(5H),10-dioxo-2H-1,2,3-triazolo[4,5-c][1]benzoazepine, or a pharmaceutically acceptable salt thereof.

3. A method according to claim 2, wherein the administration is oral administration.

4. A method according to claim 2, which comprises the administration of the effective amount of the compound together with a pharmaceutically acceptable carrier.

5. A method according to claim 2, wherein the inflammatory bowel disease is ulcerative colitis or Crohn's disease.

6. A method according to claim 1, wherein the administration is oral administration.

7. A method according to claim 1, which comprises the administration of the effective amount of the compound together with a pharmaceutically acceptable carrier.

8. A method according to claim 1, wherein the inflammatory bowel disease is ulcerative colitis or Crohn's disease.

* * * * *